(12) United States Patent
Martensson et al.

(10) Patent No.: US 11,796,464 B2
(45) Date of Patent: Oct. 24, 2023

(54) FUEL QUALITY SENSOR

(71) Applicant: Wayne Fueling Systems LLC, Austin, TX (US)

(72) Inventors: Mattias G. Martensson, Kavlinge (SE); David Dahlgren, Trollhättan (SE); Gustaf Gustafsson, Glemmingebro (SE)

(73) Assignee: Wayne Fueling Systems LLC, Austin, TX (US)

( * ) Notice: Subject to any disclaimer, the term of this patent is extended or adjusted under 35 U.S.C. 154(b) by 200 days.

(21) Appl. No.: 16/904,851

(22) Filed: Jun. 18, 2020

(65) Prior Publication Data

US 2020/0400559 A1    Dec. 24, 2020

Related U.S. Application Data

(60) Provisional application No. 62/863,359, filed on Jun. 19, 2019.

(51) Int. Cl.
*G01N 21/3577*    (2014.01)
*G01N 33/28*    (2006.01)
(Continued)

(52) U.S. Cl.
CPC .......... *G01N 21/3577* (2013.01); *G01N 1/14* (2013.01); *G01N 21/85* (2013.01);
(Continued)

(58) Field of Classification Search
CPC . F02D 19/087; F02D 2200/0611; G01N 1/14; G01N 21/314; G01N 21/3151;
(Continued)

(56) References Cited

U.S. PATENT DOCUMENTS 4,553,032 A * 11/1985 Lo ...................... G01N 21/3577
250/343
5,225,679 A * 7/1993 Clarke ............... G01N 33/2829
250/343
(Continued)

FOREIGN PATENT DOCUMENTS

DE         3712879 A1 * 11/1988   ......... G01N 33/2847
DE   102007025585 A1 * 12/2008   ......... F02D 19/0634
(Continued)

OTHER PUBLICATIONS

International Search Report and Written Opinion received for PCT Application No. PCT/US2020/038403, dated Sep. 30, 2020, 15 pages.

*Primary Examiner* — John M Zaleskas
(74) *Attorney, Agent, or Firm* — MINTZ LEVIN COHN FERRIS GLOVSKY AND POPEO, PC

(57)    ABSTRACT

A fuel quality sensor can include a pump with a suction side and a pressure side for pumping fuel along a fuel flow path between an underground reservoir and a nozzle of a fuel dispensing unit; a first transmitter disposed at the suction side of the pump on a first side of a bypass plenum in fluid communication with the fuel flow path, the first transmitter configured to transmit a first light signal at a first predetermined frequency in the bypass plenum; a receiver disposed at the suction side of the pump on a second side of the bypass plenum and configured to receive the first light signal; and a control unit electrically connected to the first transmitter and the receiver and configured to determine at least one parameter of the fuel present in the fuel flow path based on the received first light signal at the first predetermined frequency.

11 Claims, 7 Drawing Sheets

(51) Int. Cl.
*G01N 21/85* (2006.01)
*G01N 1/14* (2006.01)
*G08B 21/18* (2006.01)
*G01N 21/359* (2014.01)

(52) U.S. Cl.
CPC ..... G01N 33/2829 (2013.01); G01N 33/2847 (2013.01); G08B 21/182 (2013.01); *G01N 21/359* (2013.01); *G01N 2021/8557* (2013.01); *G01N 2201/0612* (2013.01)

(58) Field of Classification Search
CPC .. G01N 21/3577; G01N 21/359; G01N 21/85; G01N 2201/0612; G01N 2201/8557; G01N 33/2829; G01N 33/2841; G01N 33/2847; G01N 33/2852; G08B 21/182
See application file for complete search history.

(56) References Cited

U.S. PATENT DOCUMENTS

| | | | | |
|---|---|---|---|---|
| 5,239,860 A | * | 8/1993 | Harris | G01N 33/2852 250/342 |
| 5,262,645 A | * | 11/1993 | Lambert | G01N 21/3577 250/339.04 |
| 5,569,922 A | * | 10/1996 | Clarke | G01N 21/3577 250/341.5 |
| 5,750,995 A | * | 5/1998 | Clarke | G01N 21/3577 250/339.09 |
| 5,958,780 A | * | 9/1999 | Asher | G01N 33/2882 436/27 |
| 6,100,975 A | * | 8/2000 | Smith | G01N 21/65 372/92 |
| 6,237,575 B1 | * | 5/2001 | Lampert | F02D 41/0042 123/704 |
| 2008/0162016 A1 | * | 7/2008 | Lunati | F02D 41/2422 250/343 |
| 2008/0201084 A1 | * | 8/2008 | Lutnick | G06Q 99/00 702/23 |
| 2008/0204714 A1 | * | 8/2008 | Hamatani | G01N 21/85 356/72 |
| 2008/0246955 A1 | * | 10/2008 | Osaki | F02D 19/088 356/73 |
| 2010/0007874 A1 | * | 1/2010 | Lunati | F02D 19/087 356/70 |
| 2010/0157302 A1 | * | 6/2010 | Serai | G01N 21/314 356/436 |
| 2011/0161256 A1 | * | 6/2011 | Lutnick | G01N 33/2829 123/406.12 |
| 2012/0223515 A1 | * | 9/2012 | Avramescu | G01N 33/2847 280/830 |
| 2013/0112169 A1 | * | 5/2013 | Lutnick | G06Q 99/00 123/406.12 |
| 2017/0038359 A1 | * | 2/2017 | Lutnick | G06Q 99/00 |
| 2017/0314383 A1 | * | 11/2017 | Ispirescu | G01N 21/05 |
| 2019/0137474 A1 | * | 5/2019 | Lutnick | G01N 33/2829 |
| 2019/0242814 A1 | * | 8/2019 | Bachalo | G01N 33/2858 |
| 2021/0208125 A1 | * | 7/2021 | Lutnick | G06Q 99/00 |

FOREIGN PATENT DOCUMENTS

| | | | | |
|---|---|---|---|---|
| EP | 1818666 A1 | | 8/2007 | |
| EP | 2223238 A1 | | 9/2010 | |
| EP | 2495547 A1 | | 9/2012 | |
| EP | 3395756 A1 | * | 10/2018 | ............... B67D 7/04 |
| EP | 3395756 A1 | | 10/2018 | |
| EP | 3987284 A1 | | 4/2022 | |
| JP | H10329899 A | | 12/1998 | |
| JP | 2004077131 A | * | 3/2004 | ......... F02D 19/0634 |
| WO | 02/098787 A1 | | 12/2002 | |
| WO | WO-02098787 A1 | * | 12/2002 | ......... G01N 33/2847 |
| WO | 2006/013312 A1 | | 2/2006 | |
| WO | 2009061573 A1 | | 5/2009 | |
| WO | 2020257434 A1 | | 12/2020 | |

* cited by examiner

FUEL QUALITY SENSOR

CROSS REFERENCE TO RELATED APPLICATIONS

The present application claims priority to U.S. Provisional Patent Application No. 62/863,539 entitled "Fuel Quality Sensor" filed on Jun. 19, 2019, which is hereby incorporated by reference in its entirety.

FIELD

The present disclosure relates to a fuel quality sensors, and more particularly, to a fuel dispensing system with a near infrared sensor to monitor fuel quality.

BACKGROUND

A fuel dispensing system is a system installed at a gas station to pump various fuels such as gasoline, diesel, ethanol fuel, biofuels and the like into vehicles. A modern fuel dispenser can be logically divided into two main parts: an electric head section that contains an embedded computer to control the action of the pump, drive the pump's display, and communicate to an indoor sales system; and a mechanical section that includes an electric motor, pumping unit, meters, pulsers, and valves to physically pump and control the fuel flow.

One of the most important functions for the pump is to accurately measure the amount of fuel pumped and dispensed. A positive displacement flow meter is used widely to measure volumetric flow. Other techniques to measure volumetric flow or mass flow can include an angular momentum meter, a Coriolis meter, a drag force flow sensor, an electromagnetic flow sensor, a laser-doppler-anemometer (LDA), a pressure gradient technique, a thermal transport sensor, a turbine-based flow sensor, an ultrasound, and a vortex-shedding flow meter. Further, to measure contents and/or properties of the dispensed fuel, such as water content, bubbles, octane rating, density, or the like, a capacitance measuring, an electrical conductivity sensor, an electromagnetic flow sensor, a microwave absorbency, a near-infrared (NIR) spectrometry, a nuclear magnetic resonance, a thermal transport sensor, an ultrasound, or the like can be used.

Since fuel dispensers are relied on for distributing fuel to the general public, and fuel is a hazardous substance, they are subject to stringent requirements regarding safety, accuracy, and security. Typically, most jurisdictions require individual pumps to be certified for operation after installation by a certification agency.

SUMMARY

The present disclosure provides a fuel quality sensor for a fuel dispensing unit and a method for measuring a water content or air bubbles in a fuel.

In accordance with embodiments of the present disclosure, a fuel quality sensor for a fuel dispensing unit is provided and can include a pump with a suction side and a pressure side for pumping fuel along a fuel flow path between an underground reservoir and a nozzle of the fuel dispensing unit; a first transmitter disposed at the suction side of the pump on a first side of a bypass plenum, the bypass plenum in fluid communication with the fuel flow path and oriented parallel to the fuel flow path, the first transmitter configured to transmit a first light signal at a first predetermined frequency in the bypass plenum; a receiver disposed at the suction side of the pump on a second side of the bypass plenum, opposite to the first side, and configured to receive the first light signal; and a control unit electrically connected to the first transmitter and the receiver, the control unit being configured to determine at least one parameter of the fuel present in the fuel flow path based on the received first light signal at the first predetermined frequency. The determined at least one parameter can include at least one of a water content of the fuel present in the fuel flow path, a presence of air bubbles in the fuel present in the fuel flow path, and an octane rating of the fuel present in the fuel flow path.

One or more of the following features can be included in any feasible combinations. The first light signal can be a first laser diode having the first predetermined frequency. The control unit can continuously determine the at least one parameter of the fuel present in the fuel flow path. Further, the control unit can trigger an alarm and/or stop the pump in response to detecting that the established at least one parameter deviates from a predetermined threshold value for the at least one parameter.

The fuel quality sensor can include a second transmitter disposed at the suction side of the pump on the first side of the bypass plenum and configured to transmit a second light signal at a second predetermined frequency in the bypass plenum. The second light signal can be a second laser diode having the second predetermined frequency. The control unit can further establish a difference in the at least one parameter based on a comparison between the received first light signal and the received second light signal. The control unit can compare the difference in the at least one parameter with a predetermined value to measure a water content of ethanol or diesel present in the fuel flow path. The control unit can compare the difference in the at least one parameter with a predetermined value to detect the presence of air bubbles in the fuel present in the fuel flow path. The control unit can trigger an alarm and/or stop the pump in response to detecting that the difference in the at least one parameter deviates from the predetermined value.

In accordance with embodiments of the present disclosure, a fuel dispensing unit for refueling vehicles can include a fuel quality sensor disclosed herein.

In accordance with embodiments of the present disclosure, a method for determining at least one parameter of a fuel present in a fuel flow path of a fuel dispensing unit is provided and can include the steps of transmitting a first light signal at a first predetermined frequency from a first side of a bypass plenum, the bypass plenum in fluid communication with the fuel flow path and oriented parallel thereto; receiving the first light signal at a second side of the bypass plenum, the second side being opposite to the first side; determining at least one parameter of the fuel present in the fuel flow path based on the received first light signal at the first predetermined frequency, wherein the determined at least one parameter includes at least one of a water content of the fuel present in the fuel flow path, a presence of air bubbles in the fuel present in the fuel flow path, and an octane rating of the fuel present in the fuel flow path.

One or more of the following features can be included in any feasible combinations. The method can further include the steps of transmitting a second light signal at a second predetermined frequency from the first side of the bypass plenum; receiving the second light signal at the second side of the bypass plenum; and determining a difference in the at least one parameter based on a comparison between the received first light signal and the received second light signal. The fuel present in the fuel flow path can be either ethanol or diesel.

In accordance with embodiments of the present disclosure, a method for detecting at least one parameter of a fuel present in a fuel flow path of a fuel dispensing unit is provided and can include the steps of transmitting a first light signal at a first predetermined frequency from a first side of a stagnant plenum, the stagnant plenum in fluid communication with the fuel flow path and extending orthogonally away from the fuel flow path; receiving the first light signal at a second side of the stagnant plenum, the second side being opposite to the first side; determining the least one parameter of the fuel present in the fuel flow path based on the received first light signal at the first predetermined frequency, wherein the determined at least one parameter includes at least one of a water content of the fuel present in the fuel flow path, a presence of air bubbles in the fuel present in the fuel flow path, and an octane rating of the fuel present in the fuel flow path.

Notably, the present disclosure is not limited to the combination of the elements as listed above and can be assembled in any combination of the elements as described herein. Other aspects of the disclosure are disclosed infra.

BRIEF DESCRIPTION OF THE DRAWINGS

A brief description of each drawing is provided to more sufficiently understand drawings used in the detailed description of the present disclosure.

Figure 1:
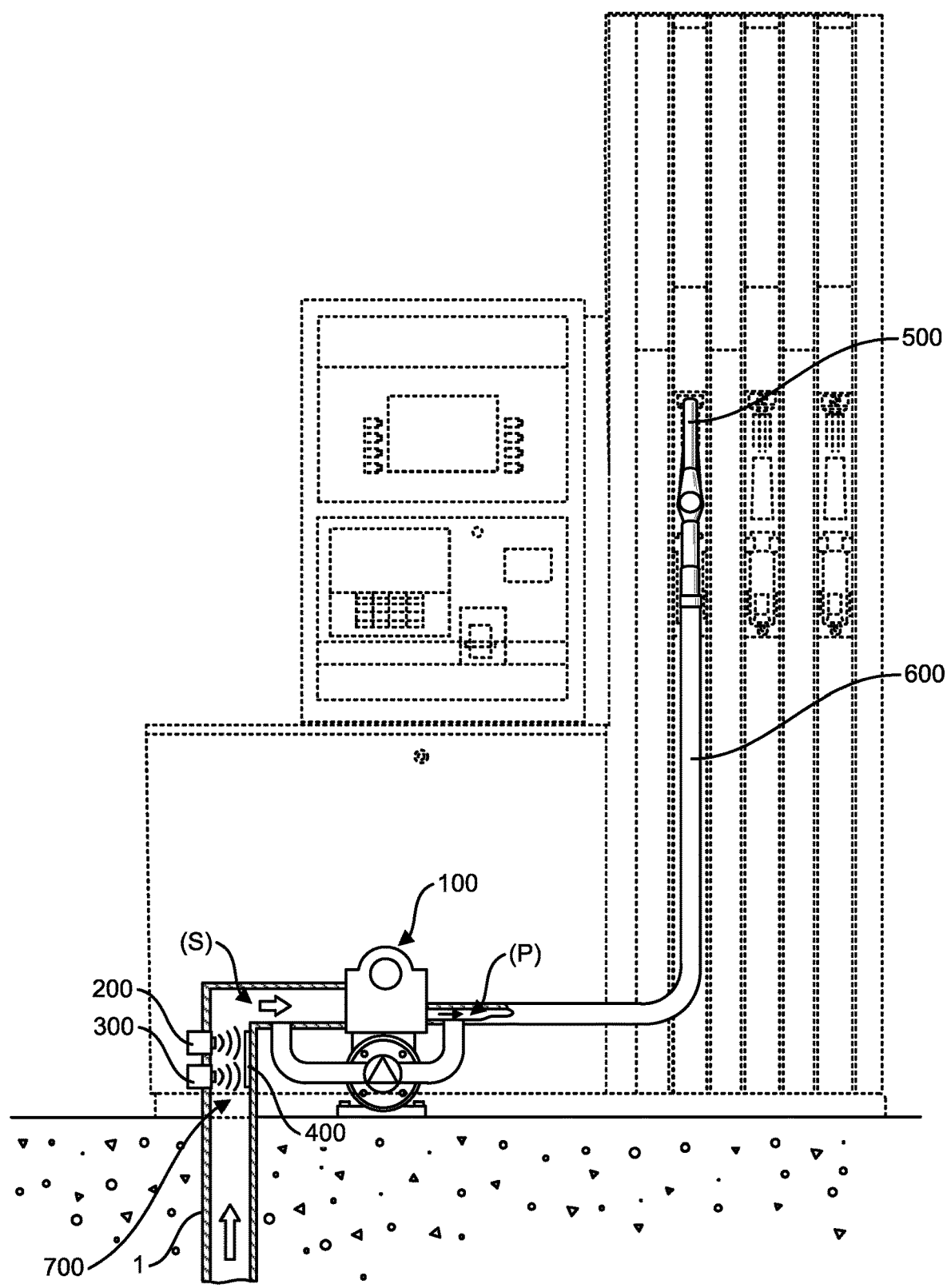
FIG. 1 illustrates a fuel dispensing unit including a fuel quality sensor with NIR according to an exemplary embodiment of the present disclosure.

It should be understood that the above-referenced drawings are not necessarily to scale, presenting a somewhat simplified representation of various features illustrative of the basic principles of the disclosure. The specific design features of the present disclosure, including, for example, specific dimensions, orientations, locations, and shapes, will be determined in part by the particular intended application and use environment.

DETAILED DESCRIPTION

Advantages and features of the present disclosure and a method of achieving the same will become apparent with reference to the accompanying drawings and exemplary embodiments described below in detail. However, the present disclosure is not limited to the exemplary embodiments described herein and can be embodied in variations and modifications. The exemplary embodiments are provided merely to allow one of ordinary skill in the art to understand the scope of the present disclosure, which will be defined by the scope of the claims. Accordingly, in some embodiments, well-known operations of a process, well-known structures, and well-known technologies will not be described in detail to avoid obscure understanding of the present disclosure. Throughout the specification, same reference numerals refer to same elements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Aspects of the present disclosure provide a fuel quality sensor for a fuel dispensing unit and a method for measuring a water content or air bubbles in a fuel. According to the present disclosure, various fuel properties can be measured accurately and reliably in real time. Due to a continuous measurement of the fuel properties such as water content, air bubbles, and octane number, the fuel pump unit can trigger an alarm when the fuel properties deviate from reference values, and thereby ensuring that the fuels with proper properties can be dispensed. Utilizing the modern photoelectronic components, the fuel pump unit according to the present disclosure can provide the above-described functionalities and advantages within a compact package at a reasonable cost with significantly improved accuracy and reliability. Moreover, the fuel pump unit according to the present disclosure can be retro-fitted to existing fuel dispensing systems with minimal alteration.

Among various techniques for measuring fuel qualities, the near-infrared (NIR) spectrometry technique provides advantages as it can measure various fuel properties in real time. Spectroscopy is a discipline that studies how matters and light interacts. It can determine content of substances by studying how they reflect or absorb light with different wavelengths. Depending on how the substance absorbs or reflect energy in the light, conclusions can be drawn about the content of the substance. In terms of measuring fuel properties, the spectrometry can determine octane number, water content, and presence of air bubbles. It can also be used to predict viscosity and density of the fuel, among others. While spectrometry can be applied with any wavelength, a near-infrared (NIR) field provides particular information for fuel properties. The NIR typically refers to the region of 780 nm to 2500 nm in the electromagnetic spectrum. NIR-spectrums can also be used to identify substances and quantities of water.

Octane rating is a property of a fuel, which tells how much compression it can withstand without auto-ignition. A higher octane number generally means higher quality of gasoline fuels. A low octane number fuel can lead to problems with a premature or uncontrolled detonation (e.g., engine knocking). The true octane number for a fuel is typically determined using a standardized motor, and requires a longer process timescale. On the other hand, determining the octane number using spectrometry can provide a faster and cheaper means. It can be used in real time and with improved precision and accuracy. A particular wavelength can be explored using laser diodes, and for example, wavelengths of 1140 nm to 1155 nm can be studied to detect different reflectance of the fuel, and thereby to determine the octane number of the fuel. Further, in order to avoid sample dependent variations such as turbidity, a comparison can be made between one measured intensity at a wavelength of interest and a normalized intensity, such as another wavelength in the same sample wavelength or pure water.

In the following description, the term frequency is used in lieu of wavenumber, but these terms have equivalent meaning. The wavenumber is the inverse of the wavelength.

Hereinbelow, a fuel quality sensor for a fuel dispensing unit according to exemplary embodiments of the present disclosure will be described in detail with reference to the accompanying drawings.

Referring to FIG. 1, which illustrates a fuel dispensing unit including a fuel quality sensor with NIR according to an exemplary embodiment of the present disclosure, a fuel dispensing unit according to an exemplary embodiment of the present disclosure can include a pump 100, one or more transmitters 200 and 300, a receiver 400, and a control unit (not shown in FIG. 1). The pump 100 can include a suction side (S) and a pressure side (P) for pumping fuel along a fuel flow path between an underground reservoir and a nozzle 500 of the fuel dispensing unit through a fuel hose 600.

Figure 2:
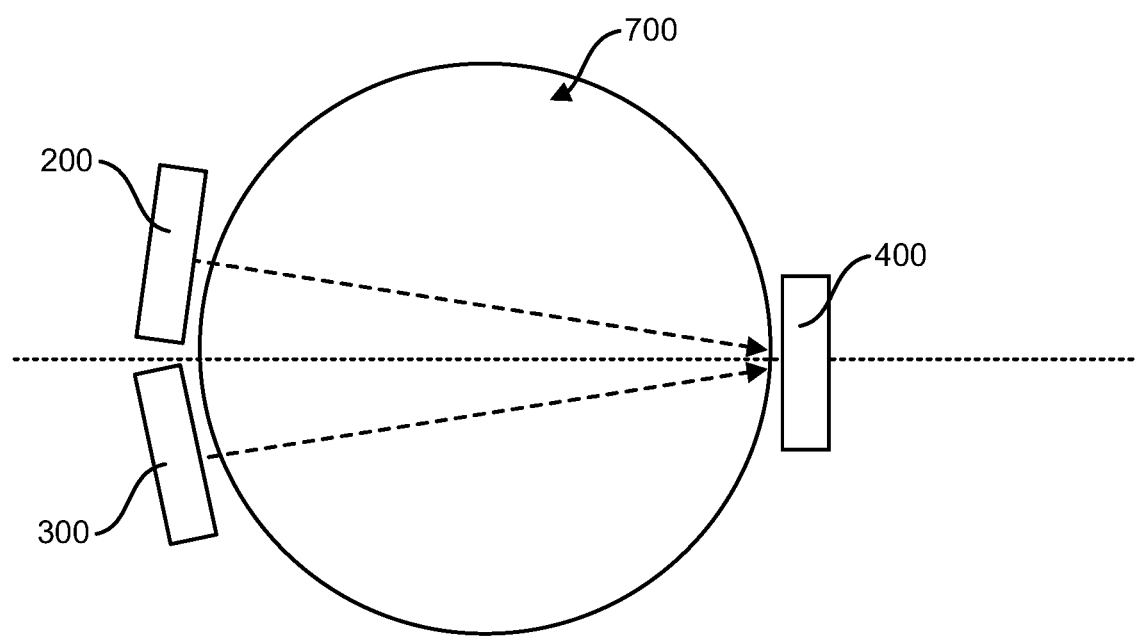
FIG. 2 illustrates an exemplary configuration of the transmitters and the receiver of the fuel quality sensor of FIG. 1 disposed at the suction side (S) of the pump in the fuel flow path according to an exemplary embodiment of the present disclosure.

FIG. 2 illustrates an exemplary configuration of the transmitters 200 and 300 and the receiver 400 of the fuel quality sensor disposed at the suction side (S) of the pump 100 in the fuel flow path 700. Referring to FIG. 2, one or more transmitters 200 and 300 can be disposed on a first side of the fuel flow path 700. A first transmitter 200 can transmit a first light signal at a first predetermined frequency in the fuel flow path or at a first range of frequencies that is the signature of one parameter to be detected. A second transmitter 300 can transmit a second light signal at a second predetermined frequency or at a first range of frequencies that is the signature one parameter to be detected. The receiver 400 can be disposed at the suction side (S) of the pump 100 to receive the light transmitted from the first transmitter 200 and/or the second transmitter 300. Accordingly, the receiver 400 can be disposed substantially opposite from the first transmitter 200 and the second transmitter 300 across the fuel flow path 700.

Each of the first transmitter 200 and the second transmitter 300 can be a light source having a coherent beam such as a laser. However, the first transmitter 200 and the second transmitter 300 are not limited to a coherent light source, and each of the first transmitter and the second transmitter can be a light source having an incoherent beam such as a light emitting diode (LED). The laser for the first transmitter 200 and the second transmitter 300 can be selected based on the required frequency, power, beam quality, form factor, or the like. The laser can be configured as a continuous wave laser or a pulse laser including, for example, a gas laser, an excimer laser, a solid-state laser, a photonic crystal laser, a semiconductor laser, a dye laser, or the like. Further, each of the first transmitter 200 and the second transmitter 300 can include a lens and/or a reflector to direct the beam to a particular direction more efficiently.

Figure 3:
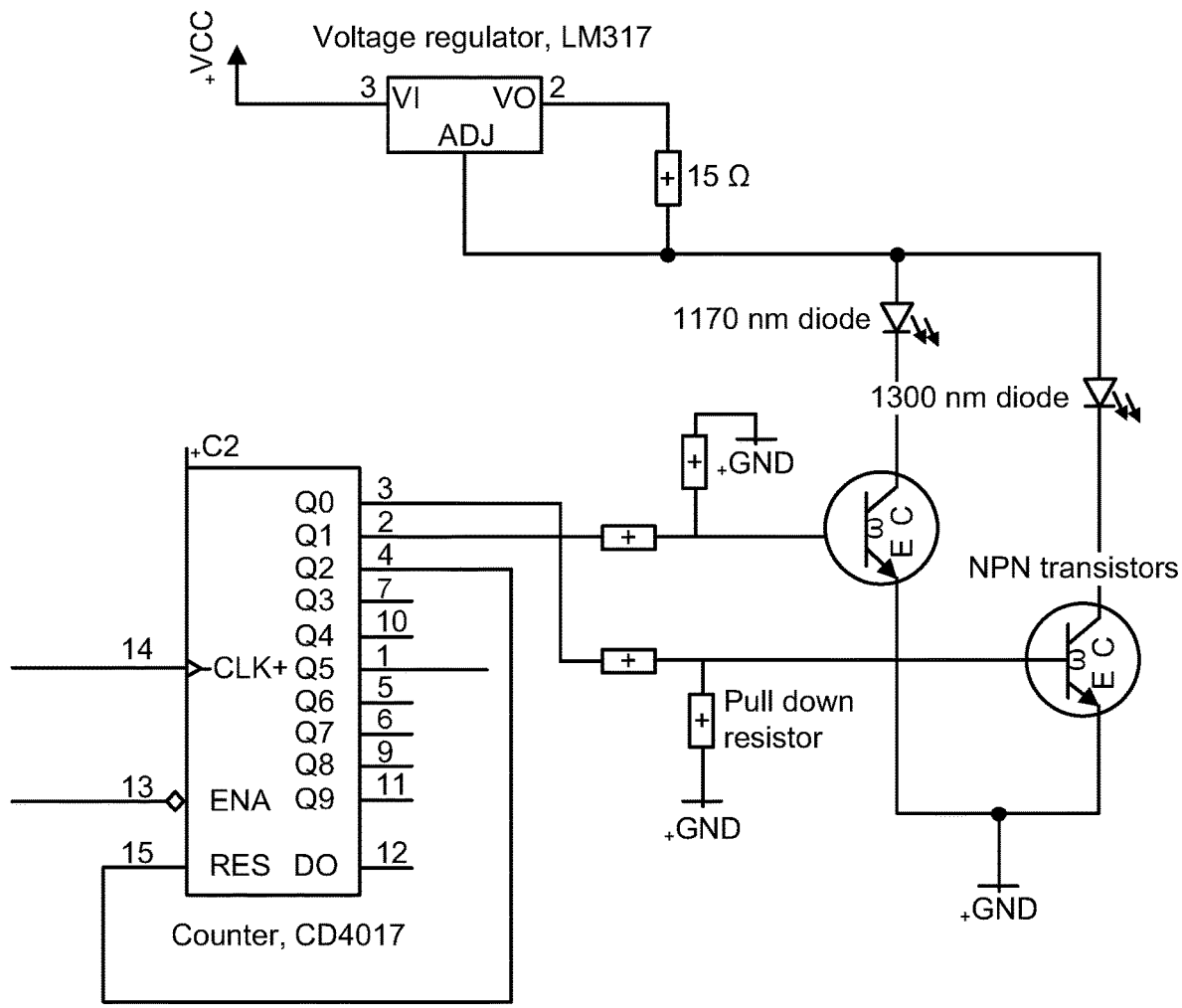
FIG. 3 shows an exemplary circuit diagram for the transmitter part of the fuel quality sensor of FIG. 1 according to an exemplary embodiment of the present disclosure.

In some implementations, each of the first transmitter 200 and the second transmitter 300 can include a light source provided with a laser diode. FIG. 3 shows an exemplary circuit diagram for the transmitter part of the fuel quality sensor. A time-division multiplexing (TDM) scheme can be used to allow the laser to alternate in emitting light with a selectable frequency. To implement the TDM scheme, a counter (e.g., CD4017) can be used to cause a current to flow through the laser diodes (e.g., 1170 nm diode and 1300 nm diode) by opening and closing the respective transistors. The counter can operate the laser diodes to continually cycle through activating a first laser diode, activating a second laser diode, and a black-out mode. The black-out period can be used to record the dark current and establish a background level (e.g., a baseline). The laser diodes can be supplied with a constant current source (e.g., LM317 voltage regulator). For example, a constant current of 83.3 mA can be supplied by connecting a 1.25 V power source with a 15Ω resistor.

Figure 4:
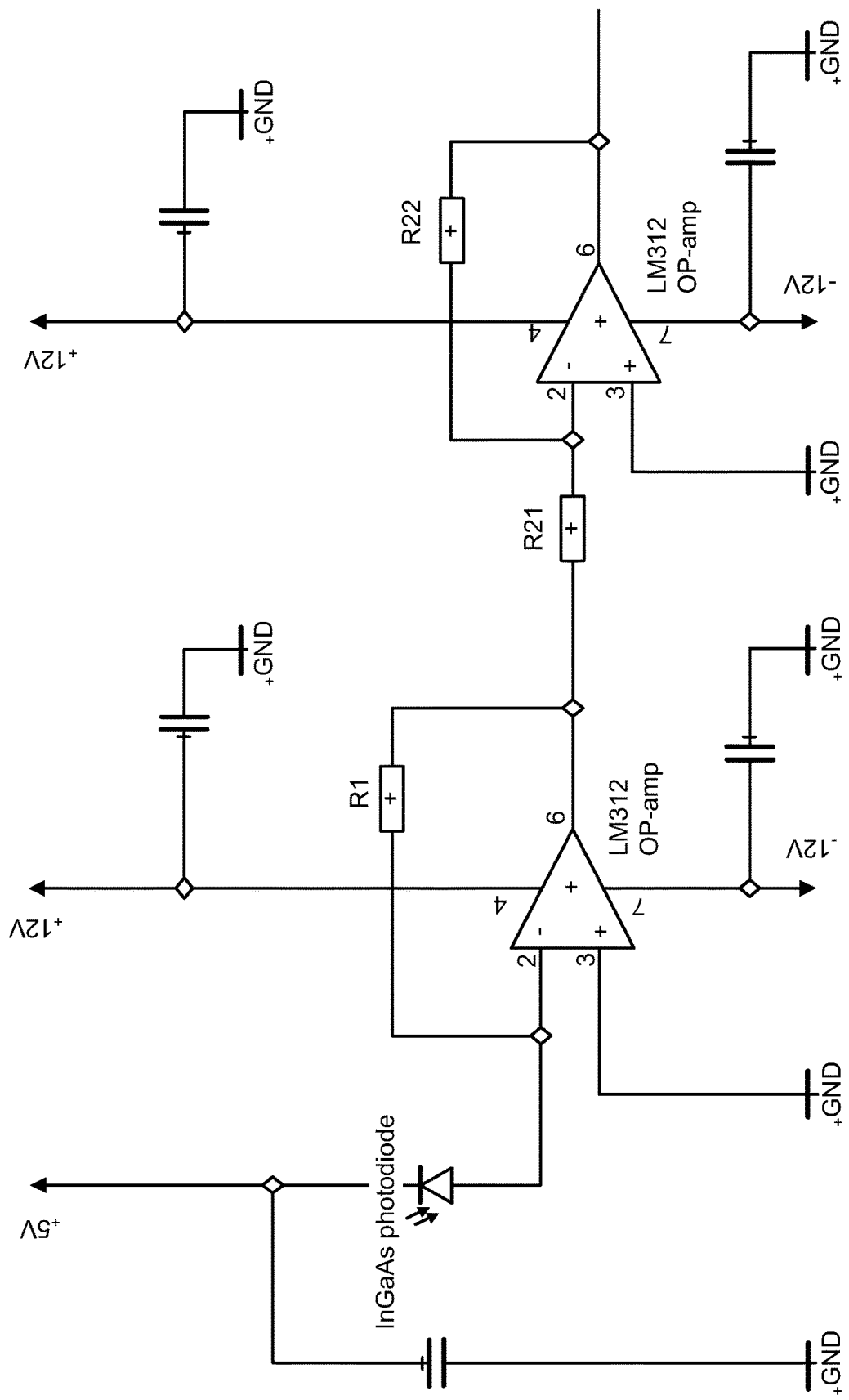
FIG. 4 shows an exemplary circuit diagram for the receiver part of the fuel quality sensor of FIG. 1 according to an exemplary embodiment of the present disclosure.

In some implementations, the receiver 400 can include a photodiode. However, the present disclosure is not limited to use of a photodiode. Any photometric devices such as photoresistor, photomultiplier, and the like can also be used. A photodiode can produce a particular current when illuminated with light. FIG. 4 shows an exemplary circuit diagram for the receiver part of the fuel quality sensor. The receiver 400 can further include an amplifier (e.g., LM312 OP-amp). The amplifier can include two or more amplification steps. In some implementations, the photodiode can be an InGaAs-based photodiode, which includes a response in the NIR range (e.g., 800 nm-2600 nm). The photodiode can also be a Si-based photodiode, which includes a response range up to about 1100 nm. The InGaAs photodiode can have a sensitivity of 0.90 A/W at 1310 nm and 0.95 A/W at 1550 nm. On the amplification side, the current generated by the photodiode can be first converted to an inverted voltage. Subsequently, the inverted voltage can be converted through an inverting amplification step.

The combination of light emitting diode with photodiode provides a compact sensor that is not sensible to vibrations due to the motor of the pumping unit.

Accordingly, at the suction side (S) of the fuel flow path 700, the first transmitter 200 and the second transmitter 300 can emit light at their respective frequencies or range of frequencies. Each of the emitted lights can travel within the fuel flow path 700 through the fuel, and can reach the receiver 400. Depending on the properties of the fuel present in the fuel flow path 700, the intensity of the light received in the receiver 400 can be changed at particular frequencies. The signal received and processed in the receiver 400 can be transmitted to the control unit.

The control unit can be electrically connected to at least one of the first transmitter 200, the second transmitter 300, and the receiver 400. The control unit can include a memory and a processor that can execute program instructions provided from the memory. The control unit can calculate relevant parameters based on the signals received and processed at the receiver 400. Herein, the parameter that the fuel dispensing unit according to the present disclosure detects, monitors, and/or calculates can include octane rating of the fuel, water content in the fuel, presence and/or quantity of air bubbles in the fuel. However, the present disclosure is not limited thereto, and the parameters to be detected, monitored, and/or calculated can vary based on the frequencies of the light sources and the algorithm implemented for data processing. The parameter can be a component or a chemical species. The frequencies can be selected as a function of the parameter or component to detect. The frequencies or wavenumbers selected are the signature of the parameter. In presence of this parameter a part of the light energy at this selected frequency is absorbed by the component in the parameter. For instance, if the parameter is water content, the wavelength used can be 1450 nm or 1930 nm because water absorbs light energy mainly at these two wavelengths. If the parameter is octane, the wavelengths are selected as a function of the octane number. Octane number varies for different kinds of gasoline. Some useful wavelengths for use in determining the octane number are between 1,000 nm and 1,600 nm. Air bubbles mean in fact a blending of air and fuel in gas phase. Carbon dioxide in air at a wavenumber of 2349 $cm^{-1}$, for instance, can be detected. As the spectral signatures of some fuel components of fuel are different while at a liquid phase or at a gaseous phase, it is possible to detect gaseous fuel inside liquid fuel.

Further, the control unit can compare the calculated parameters with a predetermined value in order to draw conclusions regarding the fuel present in the fuel flow path 700. In particular, the control unit can continuously monitor the parameter, and can trigger an alarm when the parameter deviates from the predetermined value. Additionally or alternatively to triggering the alarm, the control unit can stop the pump when the parameter deviated from the predetermined value.

In the control unit, the responses to the first frequency of the first transmitter 200 and the second frequency of the second transmitter 300 can be monitored separately and/or collectively. In some implementations, depending on the fuel property to be measured and monitored, the first frequency of the first transmitter 200 and the second frequency of the second transmitter 300 can each provide information for distinct properties. In other implementations, the responses to the first frequency of the first transmitter 200 and the second frequency of the second transmitter 300 can be monitored together to collectively indicate a single parameter. For example, to detect the octane number, an absorbance ratio can be calculated. In some implementations, the absorbance ratio can be made between a first absorbance at a wavelength of 1170 nm and a second absorbance at a wavelength of 1300 nm, each of which are respectively calculated based on the difference of the measured voltage and the black-out voltage for each of the first frequency and the second frequency that are received and amplified by the receiver 400, and the absorbance ratio can be used to determine the octane number. These two wavelengths are the spectral signature of the octane number.

The control unit can obtain the fuel parameters once (e.g., static measurement). To more effectively monitor the fuel properties using the fuel dispensing unit according to the present disclosure, the control unit can obtain the fuel parameters continuously or continually with a predetermined interval (e.g., dynamic measurement) and can measure the fuel parameters as a function of time. When the fuel parameters are measured as a function of time, any changes in the fuel property can be monitored and detected, and when a fuel parameter deviates from a predetermined reference value, the control unit can trigger an alarm to notify an operator. The alarm can be visibly displayed and/or audibly presented at the fuel pump to notify the end user customer. Additionally or alternatively, the alarm can be visibly displayed and/or audibly presented to a manager (e.g., an operating personnel) of the gas station. The alarm can be further transmitted to a fuel product provider (e.g., middle distributer) or higher in the distribution hierarchy.

The fuel dispenser comprises a suction pipe 1 connecting the fuel reservoir to the pump 100.

Figure 5A:
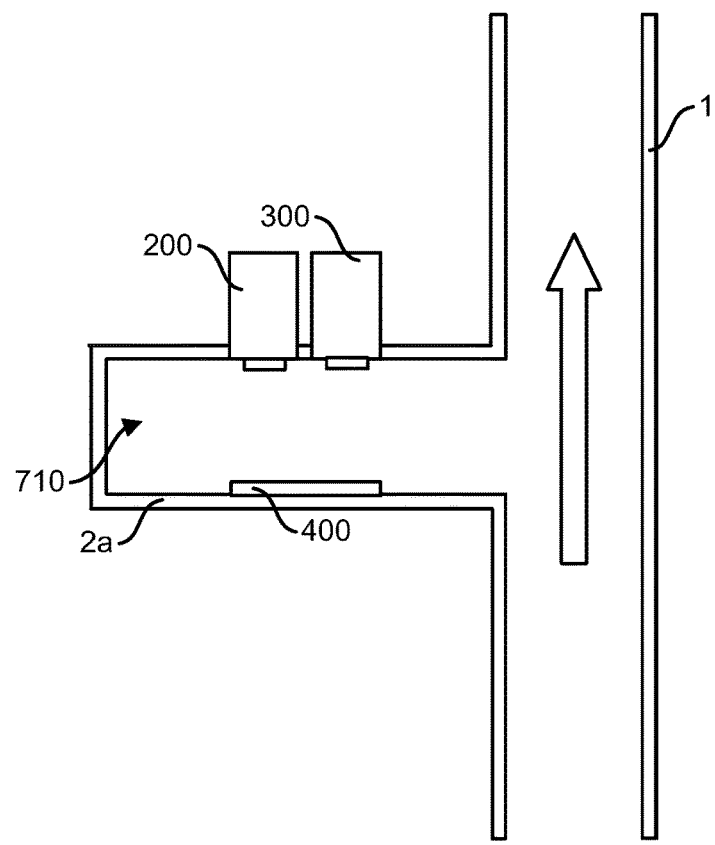
FIGS. 5A and 5B show exemplary configurations of the transmitters and the receiver of the fuel quality sensor of FIG. 1 disposed at the suction side (S) of the pump in the fuel flow path according to additional exemplary embodiments of the present disclosure.
Figure 5B:
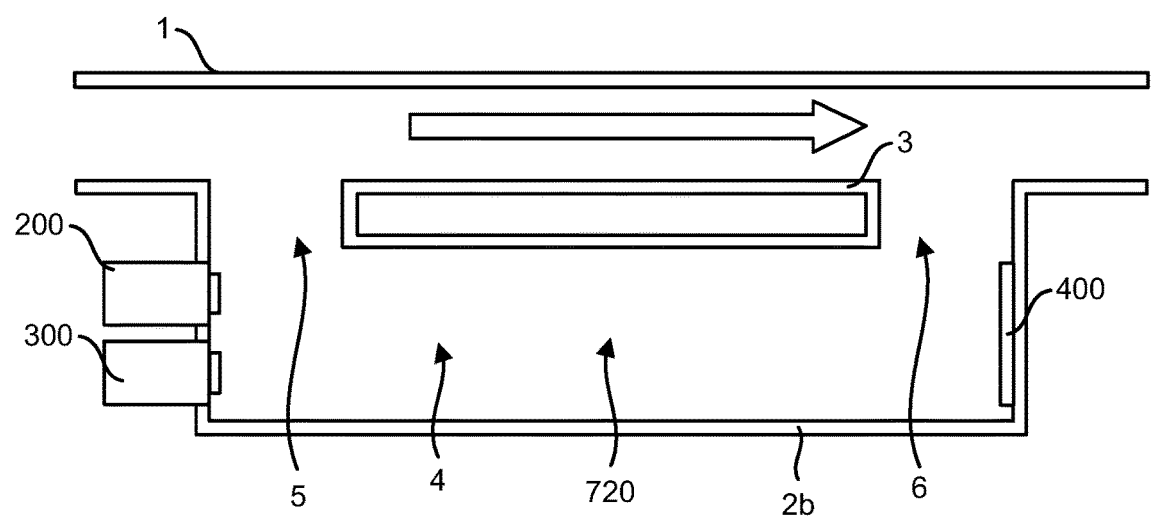

In some embodiments, as shown in FIGS. 5A and 5B, the measurement can be made at a separately provided plenum 710, 720 (e.g., a tee) to remove or decrease short-timescale variations due to, for example, turbulence or unsteadiness of the fuel flow. The plenum 710, 720 is connected to the suction pipe 1 and is in fluid communication with the suction pipe 1. The plenum 710, 720 is delimited by an enclosure 2a, 2b that could have a parallelepipedal shape, a cylindrical shape or an oval shape. Referring to FIG. 5A, a stagnant plenum 710 can be formed by teeing off from the fuel flow path 700 as a dead-end optical cavity. The stagnant plenum 710 extends perpendicularly with respect to the suction pipe 1 and is delimited by an enclosure 2a. Within the stagnant plenum 710, the fuel flow can be substantially stagnant, and the measurement can be prevented from affected by the flow unsteadiness, knowing that the classic flowrate can be up to 80 l/min. Referring to FIG. 5B, a bypass plenum 720 can provide a bypass flow parallel to the main flow in the fuel flow path 700. The bypass plenum 720 extends parallel to the suction pipe 1 and is delimited by an enclosure 2b. Within the bypass plenum 720, the flow velocity can be reduced, and the measurement can be prevented from affected by the flow unsteadiness. Moreover, in the configuration shown in FIG. 5B, the receiver 400 can be disposed axially (e.g., longitudinally) from the first transmitter 200 and the second transmitter 300. The axially arranged configuration can generally allow a longer optical path for the laser to interact with the fuel such that a detection limit and/or a signal-to-noise ratio can be improved.

In some implementations, the bypass plenum 720 is separated from the fuel flow path inside the suction pipe 1 by a wall 3. The wall 3 and the enclosure 2b defines a bypass channel 4 comprising an inlet 5 and an outlet 6. The wall 3 can be formed by a part of the suction pipe 1.

According to a possible embodiment, the enclosure 2a, 2b is part of a longitudinal pipe that is intended to be connected to the suction pipe 1. It provides a measurement unit that can be retrofitted in fuel dispensers in the field.

Further, the measurement can be taken at two or more separate locations within the fuel reservoir. In particular, a measurement unit can be disposed at or near the bottom of the fuel reservoir, and another measurement unit can be disposed at or near the top of the fuel reservoir. By comparing the measurements taken at two different locations such as top and bottom, the fuel properties variations due to stratification of the fuel can be more effectively identified. For example, since water does not mix with fuel, the water content measured at the bottom of the fuel reservoir and at the top of the fuel reservoir can be different. Accordingly, by measuring the fuel properties at two or more locations within the fuel reservoir, the measurement accuracy and reliability can be improved.

Figure 6:
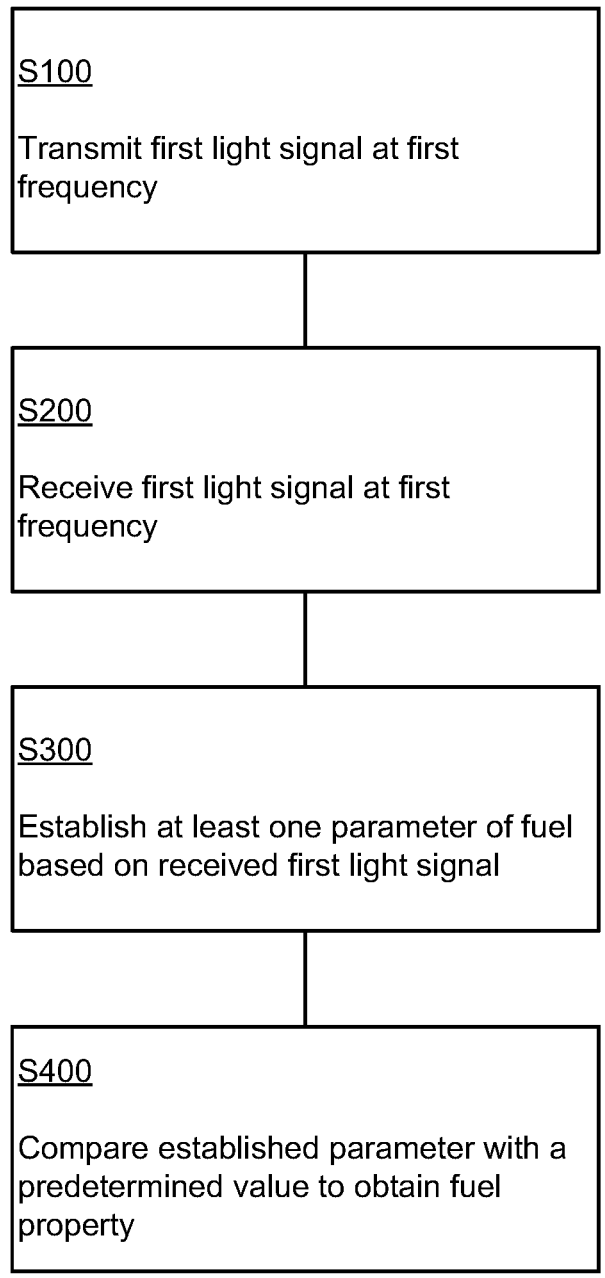
FIG. 6 shows a flow chart for monitoring the fuel quality using an NIR sensor according to an exemplary embodiment of the present disclosure.

Another aspect of the present disclosure provides a method for determining a water content or air bubbles in fuel of a fuel flow path. Referring to FIG. 6, the method for determining a water content or air bubbles can include steps of transmitting a first light signal at a first predetermined frequency from a first side of the fuel flow path (Step S100), receiving the first light signal on a second side of the fuel flow path (Step S200), and establishing at least one parameter of the fuel that is present in the fuel flow path based on the received first light signal at the first predetermined frequency (Step S300). Further, the established parameter can be compared with a predetermined value to provide information on the fuel present in the fuel flow path (Step S400). The established parameter can indicate a water content in the fuel or presence of air bubbles in the fuel or octane number.

Figure 7:
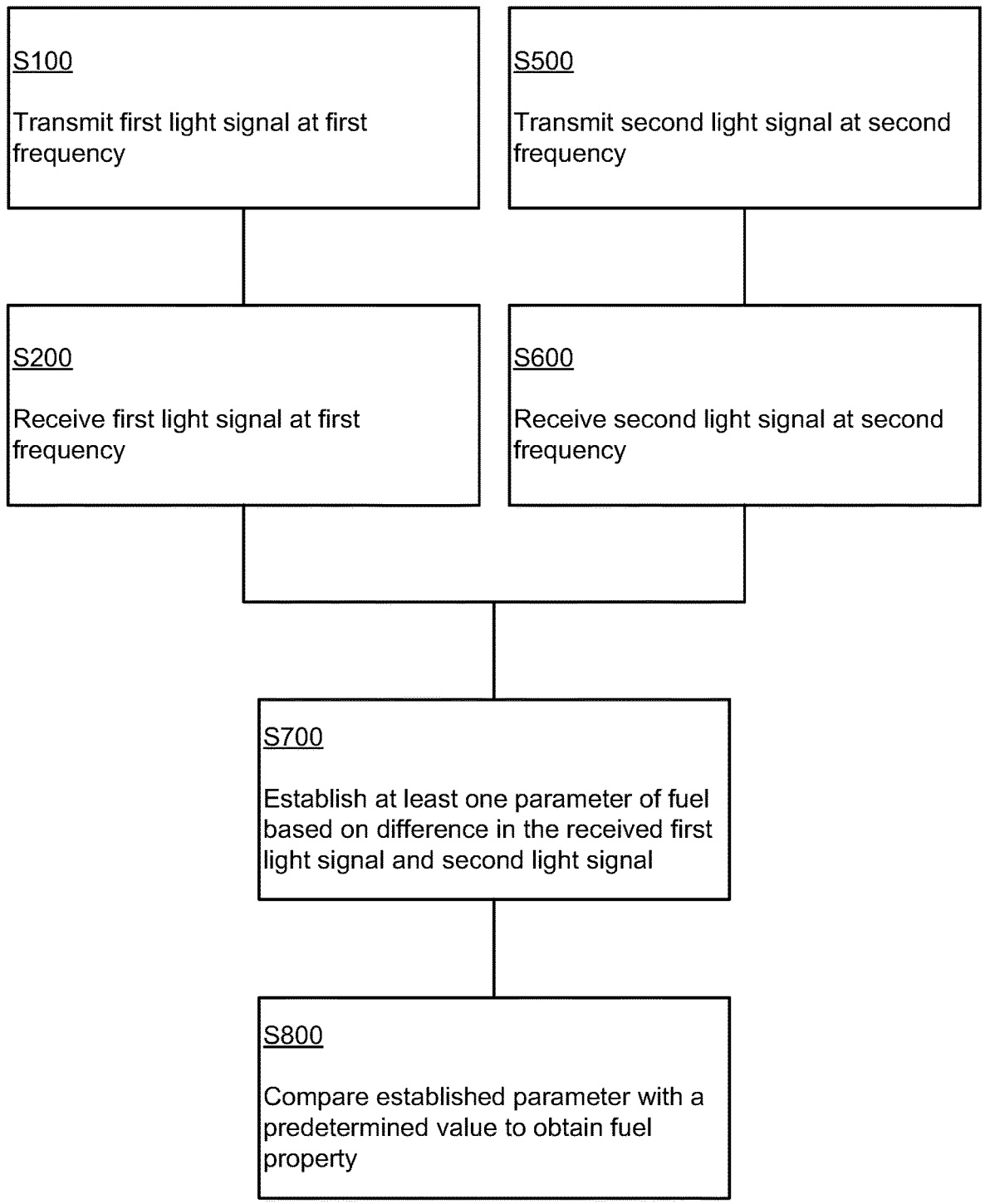
FIG. 7 shows a flow chart for monitoring the fuel quality using an NIR sensor according to an additional exemplary embodiment of the present disclosure.

Referring to FIG. 7, the method for determining water content, air bubbles and octane number in fuel of a fuel flow path can further include steps of transmitting a second light signal at a second predetermined frequency from the first side of the fuel flow path (Step S500), and receiving the second light signal on the second side of the fuel flow path (Step S600). The method can establish at least one additional parameter of the fuel that is present in the fuel flow path based on the received second light signal at the second predetermined frequency. Alternatively or additionally, the method can establish a difference in the at least one parameter based on a comparison between the received first light signal and the received second light signal (Step S700). Further, the method can compare the difference in the at least one parameter with a predetermined value in order to provide information on the fuel (Step S800). The established parameter can indicate a water content in the fuel or presence of air bubbles in the fuel.

For instance, water absorbs light energy at the wavelengths of 1450 nm and 1930 nm. First frequency can be 1450 nm, providing a first parameter of water content. Difference in the first parameter is compared with a predetermined value. Second frequency can be 1930 nm, providing a second parameter of water content. Difference in the second parameter is compared with a predetermined value for improving reliability.

Alternatively, first frequency can be 1450 nm, providing a first parameter of water content. Difference in the first parameter is compared with a predetermined value. Second frequency can be a wavelength that is the spectral signature of ethanol. Difference in the second parameter is compared with a predetermined value. If the first parameter indicates that the water rate is high, the second parameter will indicate that the ethanol rate if low confirming high water level in ethanol.

As another example relating to octane number, the first frequency could be the spectral signature of octane number of 87 providing a first parameter. The second frequency could be the spectral signature of octane number of 92 providing a second parameter. First and second parameters are compared in a fuel blending to determine a final parameter which is the octane rating of the fuel present in the fuel flow path.

In the foregoing exemplary embodiments of the present disclosure, the first side and the second side of the fuel flow path can be substantially opposite to each other. The light signal can be a coherent laser beam having a particular frequency. In some implementations, the fuel flow path can include a cross-sectional geometry of a circle. In other implementations, the cross-sectional geometry of the fuel flow path can be a square to allow the emitted light to enter the fuel flow path with less reflection or refraction along the wall-fuel interface. However, the cross-sectional geometry of the fuel flow path is not limited thereto and can be selected from any geometry. Further, the transmitters and/or the receiver can be disposed inside of the fuel flow path or outside of the fuel flow path. When the transmitters and/or the receiver are disposed outside of the fuel flow path, the walls of the fuel flow path can include an optically transparent window. The optically transparent window can be formed of silica glass, quartz, sapphire, or a transparent plastic such as polycarbonate. In some implementations, to increase the optical path length of the laser beam within the fuel flow path, one or more reflectors can be included. In spectrometry, the light absorbance or reflectance can proportionally increase with the increasing length of the optical path within the specimen. Accordingly, by including reflectors, the light emitted by the laser can be reflected multiple times within the fuel flow path to establish an increased optical path before the emitted light is received by the receiver.

In the foregoing exemplary embodiments, a configuration in which two transmitter and one receiver are arranged was described. However, the present disclosure is not limited thereto. More than two transmitters having various frequencies can be used, and moreover, more than one receiver can be included. For example, a transmitter and a receiver can be paired one to one. In some implementations, one or more laser with a tunable frequency can be included. A tunable laser can provide a wider frequency capability within a single device since the frequency of the laser can be tuned over a range of frequencies by adjusting operating parameters of the laser, such as a temperature.

In operation, due to the continuous monitoring the fuel property, the fuel dispensing unit can provide the customer with an accurate, actual blending of octane number, and thereby can allow the customer to pay based on the actual blending of octane number, not merely by the nominal octane number listed on the pump. For example, when a first customer dispenses a fuel with a nominal octane number of 87 priced at a first price, and a subsequent customer orders the dispensing unit to dispense a fuel with a nominal octane number of 92 priced at a second price, there can be a transition period over which the octane rating gradually changes from about 87 to about 92. By measuring the actual octane number in real time during the transition period as the fuel is dispensed, the price of the resulting fuel can be calculated to correspond to the actual amount of 87 octane fuel and 92 octane fuel blended in.

As set forth above, the fuel pump unit according to the present disclosure can provide accurate and reliable measurement of various fuel properties in real time. Due to a continuous measurement of the fuel properties such as water content, air bubbles, and octane number, the fuel pump unit can trigger an alarm when the fuel properties deviate from reference values, and thereby ensuring that the fuels with proper properties can be dispensed. Using a NIR spectrometry technique based on the modern photoelectronic components, the fuel pump unit according to the present disclosure can provide the above-described functionalities and advantages within a compact package at a reasonable cost with significantly improved accuracy and reliability. Moreover, the fuel pump unit according to the present disclosure can be retro-fitted to existing fuel dispensing systems with minimal alteration.

Hereinabove, although the present disclosure is described by specific matters such as concrete components, and the like, the exemplary embodiments, and drawings, they are provided merely for assisting in the entire understanding of the present disclosure. Therefore, the present disclosure is not limited to the exemplary embodiments. Various modifications and changes can be made by those skilled in the art to which the disclosure pertains from this description. Therefore, the spirit of the present disclosure should not be limited to the above-described exemplary embodiments, and the following claims as well as all technical spirits modified equally or equivalently to the claims should be interpreted to fall within the scope and spirit of the disclosure.

What is claimed is:

1. A fuel quality sensor for a fuel dispensing unit, comprising:
    a first transmitter disposed at a first side of a bypass plenum disposed at a suction side of a pump, the bypass plenum in fluid communication with a fuel flow path and oriented parallel to the fuel flow path, the first transmitter configured to transmit a first light signal at a first discrete frequency in the bypass plenum;
    a second transmitter disposed at the first side of the bypass plenum, the second transmitter configured to transmit a second light signal at a second discrete frequency in the bypass plenum;
    a receiver disposed at a second side of the bypass plenum, opposite to the first side, and configured to receive the first light signal and the second light signal; and
    a control unit electrically connected to the first transmitter, the second transmitter, and the receiver, the control unit being configured to:
        determine at least one parameter of a fuel present in the fuel flow path based on the received first light signal at the first discrete frequency and the received second light signal at the second discrete frequency,
        compare the received first light signal to the second light signal to establish a difference in the at least one parameter as characterized by each of the first and second light signals, and
        respond when the established difference in the at least one parameter deviates from a predetermined value.

2. The fuel quality sensor according to claim 1, wherein the first transmitter is a first laser diode configured to emit the first light signal at the first discrete frequency.

3. The fuel quality sensor according to claim 1, wherein the control unit is configured to continuously determine the at least one parameter of the fuel present in the fuel flow path.

4. The fuel quality sensor according to claim 3, wherein the control unit is further configured to respond by triggering an alarm or stopping the pump.

5. The fuel quality sensor according to claim 1, wherein the second light transmitter is a second laser diode configured to emit the second light signal at the second discrete frequency.

6. The fuel quality sensor according to claim 1, wherein the control unit is configured to compare the difference in the at least one parameter with the predetermined value to measure a water content of ethanol or diesel present in the fuel flow path.

7. The fuel quality sensor according to claim 1, wherein the control unit is configured to compare the difference in the at least one parameter with the predetermined value to detect a presence of air bubbles in the fuel present in the fuel flow path.

8. The fuel quality sensor according to claim 1, wherein the control unit is configured to trigger an alarm or stop the pump in response to detecting that the at least one parameter deviates from the predetermined value.

9. A method for determining at least one parameter of a fuel present in a fuel flow path of a fuel dispensing unit, comprising:
    transmitting a first light signal at a first discrete frequency from a first side of a bypass plenum, the bypass plenum in fluid communication with the fuel flow path and oriented parallel thereto;
    transmitting a second light signal at a second discrete frequency from the first side of the bypass plenum;
    receiving the first light signal and the second light signal at a second side of the bypass plenum, the second side being opposite to the first side;
    determining the at least one parameter of the fuel present in the fuel flow path based on the received first light signal at the first discrete frequency and the received second light signal at the second discrete frequency;
    comparing the received first light signal and the received second light signal to establish a difference in the at least one parameter as characterized by each of the received first and second light signals; and
    comparing the difference in the at least one parameter with a predetermined value to determine whether the difference in the at least one parameter deviates from the predetermined value.

10. The method according to claim 9, wherein the fuel present in the fuel flow path is either ethanol or diesel.

11. A method for detecting at least one parameter of a fuel present in a fuel flow path of a fuel dispensing unit, comprising:
    transmitting a first light signal at a first discrete frequency from a first side of a stagnant plenum, the stagnant plenum in fluid communication with the fuel flow path and extending orthogonally away from the fuel flow path;
    transmitting a second light signal at a second discrete frequency from the first side of the stagnant plenum;
    receiving the first light signal and the second light signal at a second side of the stagnant plenum, the second side being opposite to the first side;
    determining the at least one parameter of the fuel present in the fuel flow path based on the received first light signal at the first discrete frequency;
    comparing the received first light signal and the received second light signal to establish a difference in the at least one parameter as characterized by each of the received first and second light signals; and
    comparing the difference in the at least one parameter with a predetermined value to determine whether the difference in the at least one parameter deviates from the predetermined value.

* * * * *